(12) United States Patent
Kakiuchi et al.

(10) Patent No.: US 10,281,516 B2
(45) Date of Patent: May 7, 2019

(54) METHOD AND APPARATUS FOR INSPECTING HEAT SINK AND METHOD FOR MANUFACTURING HEAT SINK

(71) Applicant: TOYOTA JIDOSHA KABUSHIKI KAISHA, Toyota-shi (JP)

(72) Inventors: Eisaku Kakiuchi, Toyota (JP); Mitsuhiro Miura, Toyota (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 11 days.

(21) Appl. No.: 15/669,184

(22) Filed: Aug. 4, 2017

(65) Prior Publication Data

US 2018/0059165 A1 Mar. 1, 2018

(30) Foreign Application Priority Data

Aug. 24, 2016 (JP) .................. 2016-163505

(51) Int. Cl.

| B05D 1/02 | (2006.01) |
| B05D 7/14 | (2006.01) |
| G01R 31/12 | (2006.01) |
| B22D 17/22 | (2006.01) |
| B23P 15/26 | (2006.01) |
| G01N 27/20 | (2006.01) |

(52) U.S. Cl.
CPC ........... *G01R 31/1263* (2013.01); *B05D 1/02* (2013.01); *B05D 7/14* (2013.01); *B22D 17/2236* (2013.01); *B23P 15/26* (2013.01); *G01N 27/205* (2013.01); *B23P 2700/10* (2013.01)

(58) Field of Classification Search
CPC .... G01R 31/1263; G01N 27/205; B05D 1/02; B05D 7/14; B22D 17/2236; B23P 15/26; B23P 2700/10
USPC .................................... 324/426, 557
See application file for complete search history.

(56) References Cited

U.S. PATENT DOCUMENTS

2016/0103187 A1 4/2016 Itoh et al.

FOREIGN PATENT DOCUMENTS

| DE | 10 2005 016 065 A1 | 10/2006 | |
| JP | 57-202683 | 12/1982 | |
| JP | 9-252068 A | 9/1997 | |
| JP | H09252068 | * 9/1997 | ........... H01L 23/473 |
| JP | 2011-141169 A | 7/2011 | |

* cited by examiner

*Primary Examiner* — Farhana A Hoque
(74) *Attorney, Agent, or Firm* — Oblon, McClelland, Maier & Neustadt, L.L.P.

(57) ABSTRACT

Provided is a method for inspecting a heat sink that enables an accurate inspection of an insulating film formed on a surface of heat sink fins. The method including a metallic housing that includes a plurality of cooling fins arranged side by side on an outer surface thereof, and an insulating film formed on a surface of the cooling fins and between the cooling fins. The method includes disposing, in an electrolyte solution, an inspection electrode including a plurality of electrode fins insertable between the cooling fins to face the housing with a predetermined distance therebetween in such a way that the cooling fins and the electrode fins are alternately arranged; and applying a voltage between the housing and the inspection electrode, which are arranged to face each other, and inspecting a formation state of the insulating film based on a measured value of a current.

7 Claims, 17 Drawing Sheets

METHOD AND APPARATUS FOR INSPECTING HEAT SINK AND METHOD FOR MANUFACTURING HEAT SINK

CROSS REFERENCE TO RELATED APPLICATIONS

This application is based upon and claims the benefit of priority from Japanese patent application No. 2016-163505, filed on Aug. 24, 2016, the disclosure of which is incorporated herein in its entirety by reference.

BACKGROUND

The present invention relates to a method and an apparatus for inspecting a heat sink and a method for manufacturing a heat sink. A heat sink made of a metal with high thermal conductivity is known. Japanese Unexamined Patent Application Publication No. 57-202683 discloses a heat sink made of aluminum, in which a heat radiation surface thereof is covered with a fluororesin.

SUMMARY

The inventors have developed a heat sink 103 having a shape shown in FIG. 14. The heat sink 103 includes a metallic housing 108 including a plurality of fins 108a arranged in a comb-like manner on an outer surface thereof and an insulating film 109 having excellent heat dissipation properties that is formed on the surface of the fins 108a and between the fins 108a. If there is a defect in the insulating film 109, the cooling performance of the heat sink 103 is deteriorated. Therefore, it is necessary to inspect a formation state of the insulating film 109 during the process of manufacturing the heat sink 103.

The inventors inspected the heat sink 103 using an inspection apparatus 130 shown in FIGS. 15 and 16 in order to inspect the formation state of the insulating film 109. FIG. 15 is a side view showing a schematic structure of the inspection apparatus 130. FIG. 16 is a drawing seen from the direction indicated by an arrow J in FIG. 15. The inspection apparatus 130 includes an inspection tank 131, an inspection electrode 132, an electrode terminal 133, a power supply 134, and an ammeter 135. The inspection tank 131 contains an electrolyte solution 136. The shape of the inspection electrode 132 is a flat plate or a round bar. The electrode terminal 133 is attached to a non-coated part 110 (see FIG. 14) where the insulating film 109 is not formed on the housing 108.

In the inspection of the heat sink 103, firstly, the heat sink 103 and inspection electrode 132 are arranged in the inspection tank 131 in such a way that distal ends of the fins 108a and inspection electrode 132 face each other in the electrolyte solution 136. Then, a voltage is applied between the housing 8 and the inspection electrode 132 by the power supply 134, and the formation state of the insulating film 109 is inspected based on a current generated at that time.

When there is a defect in the insulating film 109, and thus the underlying metal part (surface of the housing 108) is exposed, a current flows between the exposed underlying metal part and the inspection electrode 132 through the electrolyte solution 136. If an area of the underlying metal part exposed due to the defect in the insulating film 109 is relatively large, the current flowing between the exposed underlying metal part and the inspection electrode 132 becomes relatively large. On the other hand, if the area of the underlying metal part exposed due to the defect in the insulating film 109 is relatively small, the current flowing between the exposed underlying metal part and the inspection electrode 132 becomes relatively small.

Commonly, when a voltage is applied between electrodes immersed in an electrolyte solution, the greater the distance between the electrodes, the lower the current value generated when the voltage is applied between the electrodes tends to become. Therefore, if the distance between the exposed underlying metal part and the inspection electrode 132 is relatively short, the current flowing between the exposed underlying metal part and the inspection electrode 132 becomes relatively large. On the other hand, if the distance between the exposed underlying metal part and the inspection electrode 132 is relatively long, the current flowing between the exposed underlying metal part and the inspection electrode 132 becomes relatively small. If the distance between the exposed underlying metal part and the inspection electrode 132 is much longer than a distance predetermined for proper detection of defects, the current flowing between the exposed underlying metal part and the inspection electrode 132 through the electrolyte solution 136 becomes weak. Thus, in this case, defects cannot be accurately detected by the ammeter 135.

When the heat sink 103 is inspected by using the inspection apparatus 130, a facing surface 132a of the inspection electrode 132 can be brought close to the distal end parts of the fins 108a with the predetermined distance interposed therebetween, but the facing surface 132a of the inspection electrode 132 cannot be brought sufficiently close to gap bottom parts 108b between the fins 108a. FIG. 17 is an enlarged view of a region C in FIG. 16. As shown in FIG. 17, even when the distance between the distal end parts of the fins 108a and the inspection electrode 132 is set to a predetermined distance d101, the distance between the gap bottom parts 108b and the inspection electrode 132 becomes a distance d102, which is longer than the predetermined distance d101.

When the distance between the distal end parts of the fins 108a and the inspection electrode 132 is the predetermined distance d101, if there is a defective part where the underlying metal is exposed at the distal end parts of the fins 108a, the current flowing between the exposed underlying metal part and the inspection electrode 132 can be accurately detected by the ammeter 135. On the other hand, as the distance between the gap bottom parts 108b and the inspection electrode 132 is d102 (d102>d101), even if there is a defective part where the underlying metal is exposed in the gap bottom parts 108b, the current flowing between the exposed underlying metal parts and the inspection electrode 132 becomes weak. Thus, in this case, the defective part may not be accurately detected by the ammeter 135.

In order to inspect the insulating film 109, for example, a visual inspection apparatus equipped with a high pixel camera of five million pixels. That is, the insulating film 109 is photographed by the camera, and image processing for detecting defects is performed on the photographed image to thereby detect individual defects generated in the insulating film 109. Then, the detected individual defects are evaluated as to whether or not they are at a level that affects the cooling performance of the heat sink 103. Based on a result of the evaluation, evaluation processing for evaluating the formation state of the insulating film 109 is performed. However, since the defect, which causes a problem to arise, is very small, it takes a lot of time for performing the detection and evaluation processing in the inspection of the heat sink using the visual inspection apparatus. In order to reduce the time taken for performing the detection and evaluation processing, it is necessary to introduce a highly functional processing apparatus, which increases introduction cost.

In view of the above background, an object of the present invention is to provide a method for manufacturing a heat sink that enables an accurate inspection of a formation state of an insulating film formed on a surface of fins and between the fins of the heat sink while reducing the cost.

In an example aspect of the present invention, a method for inspecting a heat sink including a metallic housing including: a plurality of first fins arranged side by side on an outer surface thereof; and an insulating film formed on a surface of the first fins and between the first fins. The method includes disposing, in an electrolyte solution, an inspection electrode including a plurality of second fins insertable between the first fins to face the housing with a predetermined distance therebetween in such a way that the first fins and the second fins are alternately arranged; and applying a voltage between the housing and the inspection electrode, which are arranged to face each other, and inspecting a formation state of the insulating film based on a measured value of a current.

By disposing the inspection electrode including the plurality of second fins insertable between the first fins to face the housing in such a way that the first fins and the second fins are alternately arranged, distal ends of the second fins, which are a part of the inspection electrode, can be brought close to bottoms between the first fins of the housing, in order to conduct an inspection. Thus, when there is a defect in the bottoms between the first fins or in side surfaces of the first fins, it is possible to accurately detect the value of the current flowing between a part where the surface of the housing is exposed, which is the defect, and the second fins. It is therefore possible to accurately inspect the formation state of the insulating film and to reduce the cost as compared with the inspection method that detects individual defects using a visual inspection apparatus.

Moreover, in the above method for inspecting the heat sink, a distance between the first fins and the second fins is changed when the voltage is applied between the housing and the inspection electrode that are arranged to face each other.

When a distance between one side surface of the first fins and one side surface of the second fins is changed such that the distance becomes smaller, if there is a defect generated in the one side surface of the first fins, the value of the current flowing between a part where the surface of the housing is exposed, which is the defect, and the second fins can be accurately detected.

When a distance between the other side surface of the first fins and the other side surface of the second fins is changed such that the distance becomes smaller, if there is a defect generated in the other side surface of the first fins, the value of the current flowing between a part where the surface of the housing is exposed, which is the defect, and the second fins can be accurately detected. It is therefore possible to accurately detect the defect in the side surfaces of the first fins.

In another example aspect of the present invention, an inspection apparatus for a heat sink including a metallic housing that includes a plurality of first fins arranged side by side on an outer surface thereof, and an insulating film formed on a surface of the first fins and between the first fins. The inspection apparatus includes: an inspection electrode including a plurality of second fins insertable between the first fins; and an ammeter configured to measure a value of a current flowing between the housing and the inspection electrode. In an electrolyte solution, the inspection electrode is disposed to face the housing with a predetermined distance therebetween in such a way that the first fins and the second fins are alternately arranged, a voltage is applied between the housing and the inspection electrode, and a formation state of the insulating film is inspected based on a measured value of a current. In the above inspection apparatus for a heat sink, by disposing the inspection electrode including the plurality of second fins insertable between the first fins to face the housing in such a way that the first fins and the second fins are alternately arranged, distal ends of the second fins, which are a part of the inspection electrode, can be brought close to bottoms between the first fins of the housing, in order to conduct an inspection. When the distal ends of the second fins are brought close to the bottoms between the first fins to conduct the inspection, when there is a defect in the bottoms between the first fins or in side surfaces of the first fins, it is possible to accurately detect the value of the current flowing between a part where the surface of the housing is exposed, which is the defect, and the second fins. It is therefore possible to accurately detect the defect in the side surfaces of the first fins.

In another example aspect of the present invention, a method for manufacturing a heat sink including a metallic housing that includes a plurality of first fins arranged side by side on an outer surface thereof, and an insulating film formed on a surface of the first fins and between the first fins. The method includes: forming the housing; forming the insulating film on the surface of the first fins and between the first fins; disposing, in an electrolyte solution, an inspection electrode including a plurality of second fins insertable between the first fins to face the housing with a predetermined distance therebetween in such a way that the first fins and the second fins are alternately arranged; and applying a voltage between the housing and the inspection electrode, which are arranged to face each other, and inspecting a formation state of the insulating film based on a measured value of a current. In the method for manufacturing the heat sink, as described above, by conducting the inspection of the heat sink capable of accurately inspecting the formation state of the insulating film while reducing the cost, it is possible to manufacture a heat sink with a satisfactory formation state of the insulating film without causing a significant increase in inspection cost.

According to the present invention, it is possible to accurately inspect the formation state of the insulating film formed on the surface of the fins and between the fins of the heat sink while reducing cost.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

Hereinafter, an embodiment of the present invention will be described with reference to the drawings.

Firstly, a schematic structure of a heat sink according to this embodiment will be described.

Figure 1:
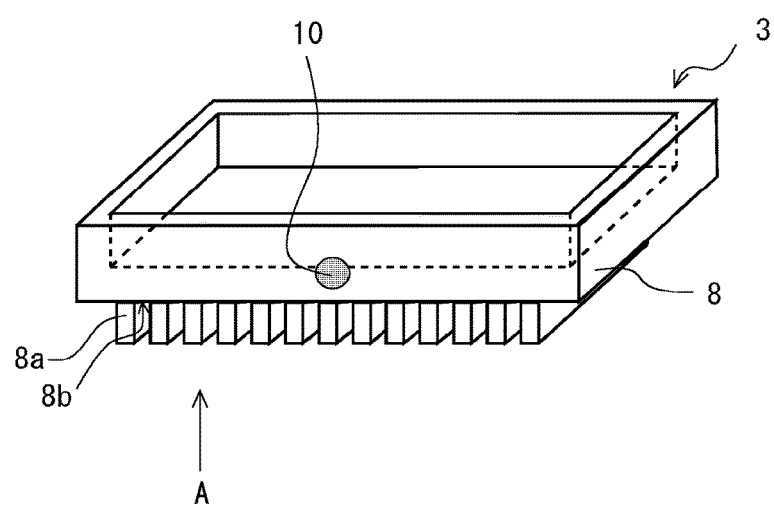
FIG. 1 is a perspective view showing a schematic structure of a heat sink.
Figure 2:
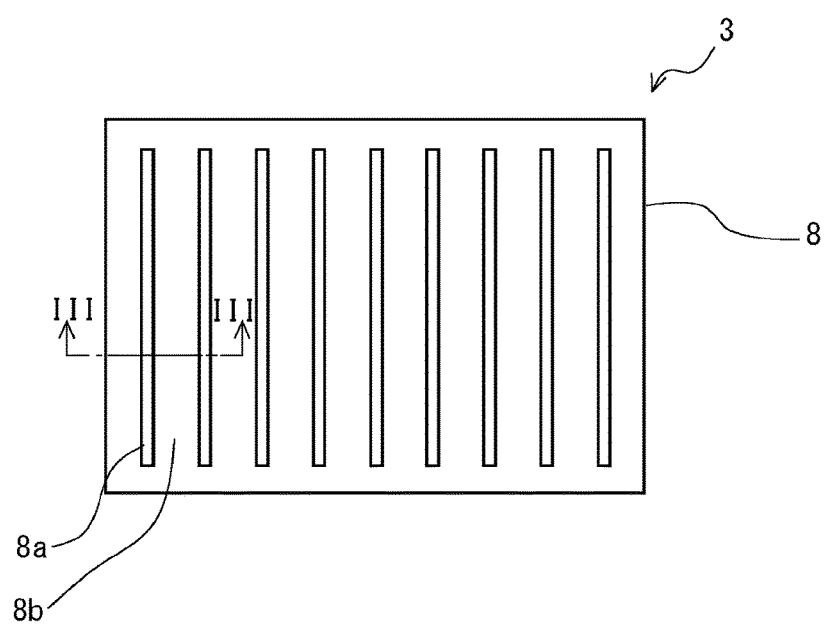
FIG. 2 is a drawing as seen from the direction indicated by an arrow A in FIG. 1.
Figure 3:
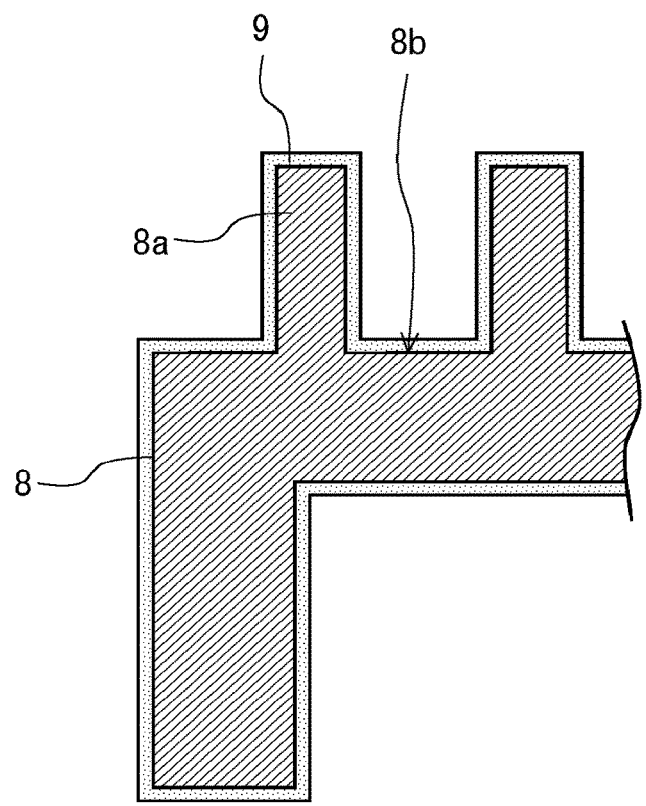
FIG. 3 is a cross-sectional diagram taken along the line of FIG. 2.

FIG. 1 is a perspective view showing a schematic structure of the heat sink 3. FIG. 2 is a drawing as seen from the direction indicated by an arrow A in FIG. 1. FIG. 3 is a cross-sectional diagram taken along the line III-III of FIG. 2. As shown in FIGS. 1 to 3, the heat sink 3 includes a metallic housing 8 including a plurality of cooling fins (first fins) 8a arranged side by side on an outer surface thereof and an insulating film 9 formed on a surface of the cooling fins 8a and in gap bottom parts 8b between the cooling fins 8a. In this embodiment, the cooling fins 8a are arranged in a comb-like manner.

The housing 8 is formed of a metal material having excellent thermal conductivity, such as aluminum, copper, or an alloy containing these as its main component. Note that the insulating film 9 is formed on the entire surface of the housing 8 shown in FIG. 3 excluding a non-coated part 10 to which an electrode terminal is attached for an inspection of the heat sink 3, which will be described later. The non-coated part 10 is formed at a part that does not affect the cooling performance of the heat sink 3. The material of the insulating film 9 may be a nitride, a resin, or the like having excellent heat dissipation properties.

Next, a schematic structure of a DC/DC converter to which the above-described heat sink 3 is applied will be described.

Figure 4:
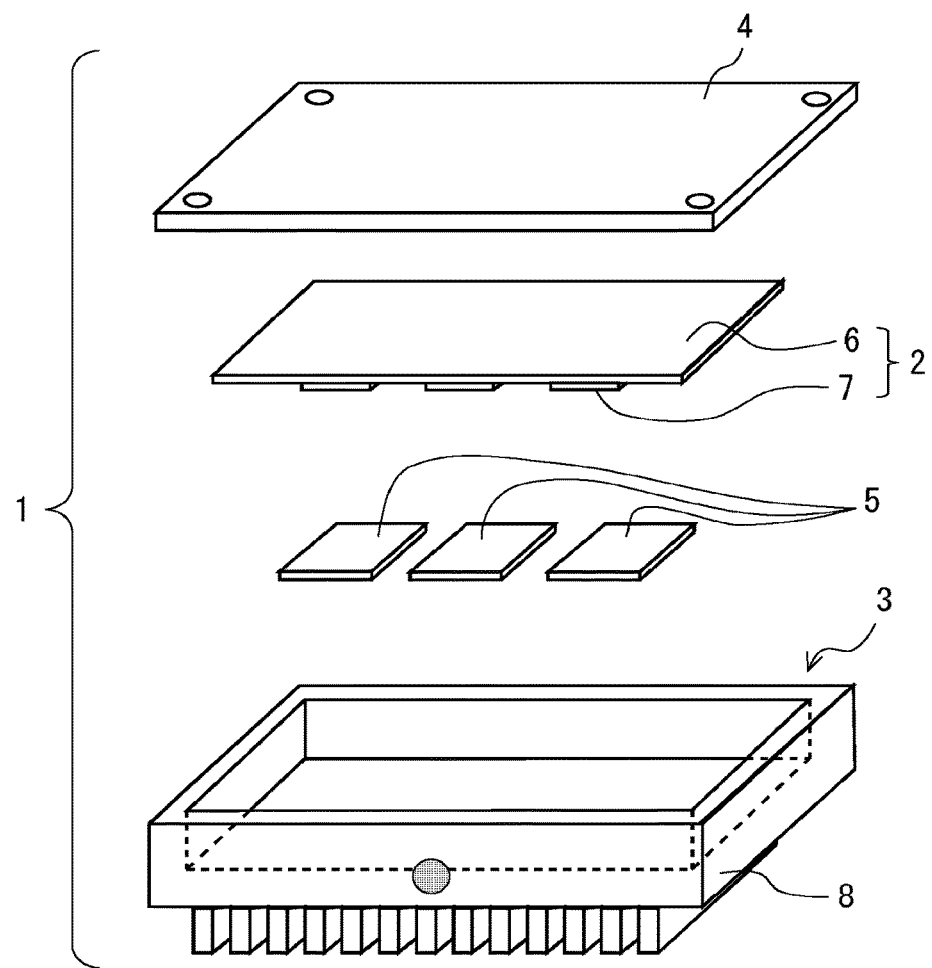
FIG. 4 is an exploded perspective view showing a schematic structure of a DC/DC converter including a heat sink according to an embodiment.

FIG. 4 is an exploded perspective view showing the schematic structure of the DC/DC converter 1. As shown in FIG. 4, the DC/DC converter 1 includes a switching electric circuit unit 2, the heat sink 3, a cover 4, and high thermal conductive resin cushion members 5. The electric circuit unit 2 includes a substrate 6 and electronic components 7 attached to the substrate 6.

The electric circuit unit 2 is accommodated inside the housing 8 of the heat sink 3. The high thermal conductive resin cushion members 5 are disposed between the electronic components 7 and an inner surface of the housing 8 so as to fill a gap generated between the electronic components 7 and the inner surface of the housing 8. The high thermal conductive resin cushion members 5 transmit heat generated in the electric components 7 to the housing 8. The high thermal conductive resin cushion members 5 are formed of a resin material having excellent thermal conductivity.

Figure 5:
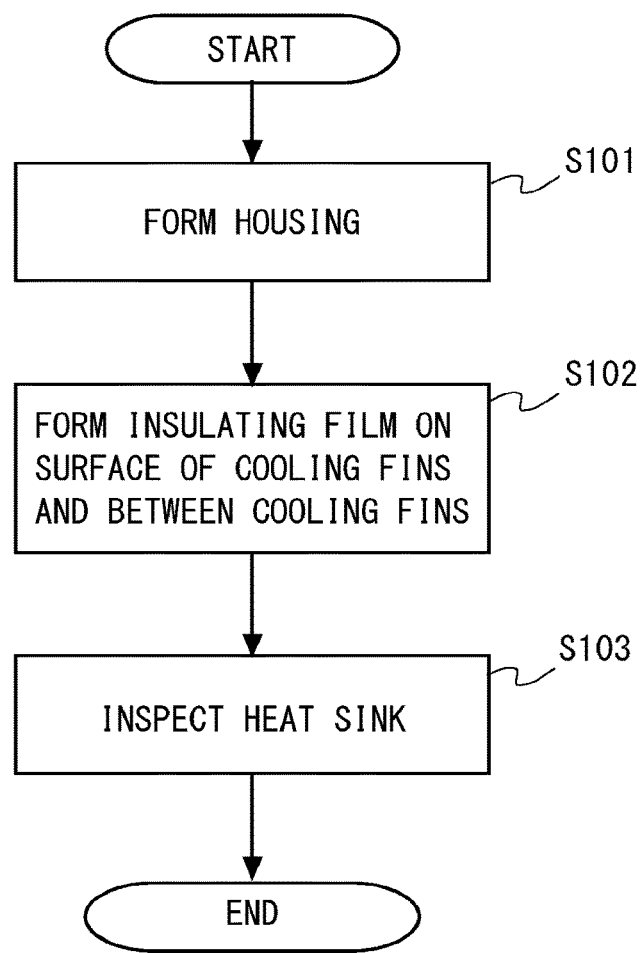
FIG. 5 is a flowchart showing a flow of a method for manufacturing a heat sink according to the embodiment.

Next, an outline of a method for manufacturing the heat sink 3 will be described with reference to FIG. 5. FIG. 5 is a flowchart showing a flow of the method for manufacturing the heat sink 3. In the following description regarding the structure of the heat sink 3, see FIGS. 1 to 3 as appropriate.

As shown in FIG. 5, the housing 8 is formed first (step S101). The housing 8 is formed by, for example, casting, forging, machining, or the like. Commonly, the housing 8 is formed by die casting. Die-casting includes a mold clamping step for clamping a moldable separable casting mold, a casting step of pouring molten metal such as molten aluminum into the mold-clamped casting mold, and a mold casting removing step for opening the mold-clamped casting mold after a temperature of the molten metal inside the mold-clamped casting mold becomes low and removing a mold inside the mold using an eject pin. Next, an insulating material is applied by spraying or the like to the surface of the cooling fins 8a and the gap bottom parts 8b between the cooling fins 8a in order to form the insulating film 9 (Step S102). Then, the heat sink 3 is inspected (step S103)

Next, the inspection performed on the heat sink 3 in Step S103 of FIG. 5 will be described in detail. Note that in the following description, FIGS. 1 to 3 will be referred to as appropriate.

If a defect such as a pinhole is generated in the insulating film 9 formed on the surface of the cooling fins 8a and in the gap bottom parts 8b between the surface of the cooling fins 8a, the cooling capability of the heat sink 3 is reduced. For this reason, it is necessary to inspect the formation state of the insulating film 9 in the heat sink 3.

Figure 6:
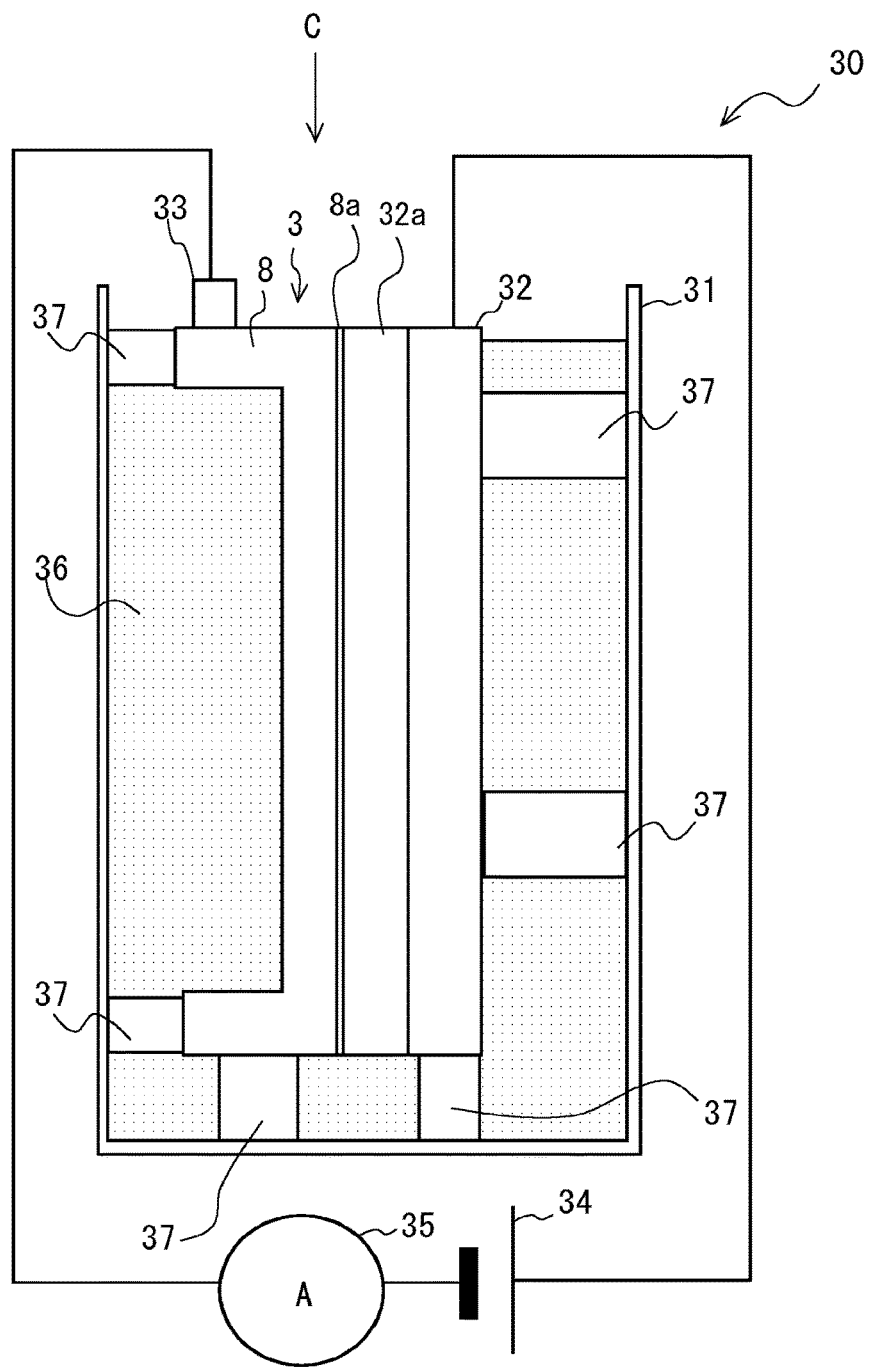
FIG. 6 is a side view showing an example of a schematic structure of an inspection apparatus for a heat sink according to the embodiment.
Figure 7:
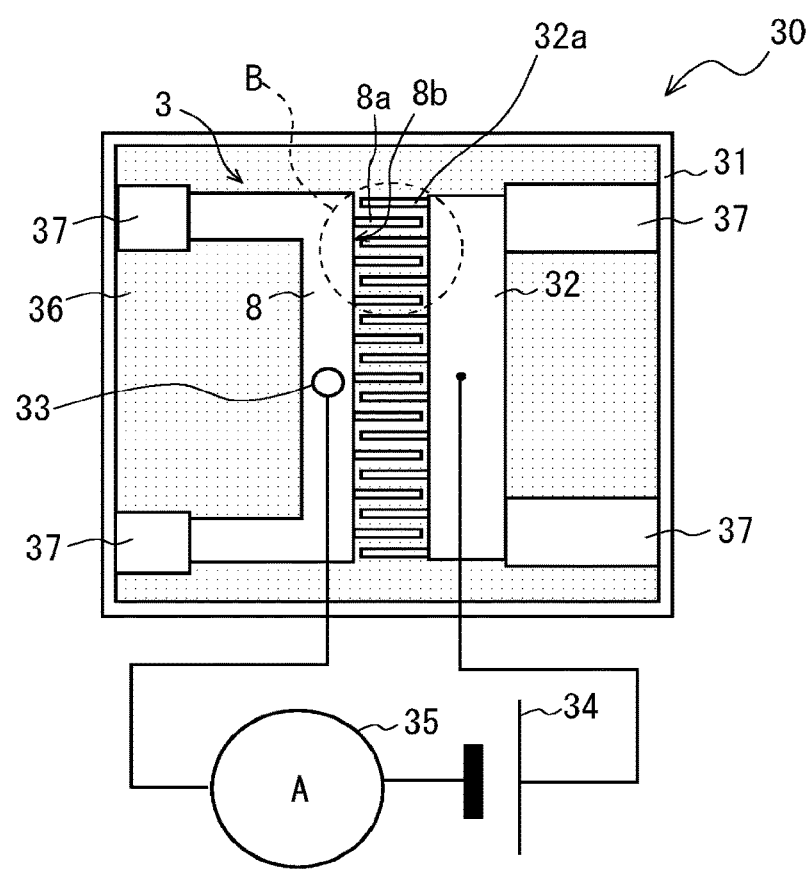
FIG. 7 is a drawing as seen from the direction indicated by an arrow C in FIG. 6.

FIG. 6 is a side view showing an example of a schematic structure of an inspection apparatus 30 of the heat sink 3. FIG. 7 is a drawing as seen from the direction indicated by an arrow C in FIG. 6. As shown in FIGS. 6 and 7, the inspection apparatus 30 includes an inspection tank 31, an inspection electrode 32, an electrode terminal 33, a power supply 34, and an ammeter 35. The inspection tank 31 contains an electrolyte solution 36 such as alum ($AlKSO_4$) or the like. In the inspection electrode 32, a plurality of electrode fins (second fins) 32a that can be inserted between the cooling fins 8a are arranged side by side.

The electrode terminal 33 is attached to the non-coated part 10 (see FIG. 1) of the housing 8 where the insulating film 9 is not formed. The power supply 34 is a direct current power supply, and the inspection electrode 32 is connected to one pole and the electrode terminal 33 is connected to the other pole. The ammeter 35 measures a current flowing between the housing 8 and the inspection electrode 32.

Figure 8:
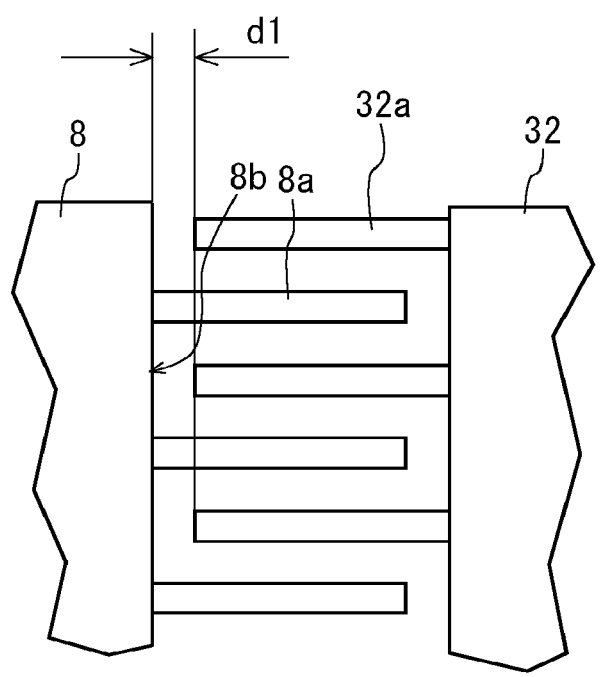
FIG. 8 is an enlarged view of a region B in FIG. 7.

FIG. 8 is an enlarged view of a region B in FIG. 7. As shown in FIG. 8, the inspection electrode 32 is disposed to face the housing 8 in the electrolyte solution 36 with a predetermined distance d1 therebetween in such a way that the cooling fins 8a and the electrode fins 32a are alternately arranged. The heat sink 3 and inspection electrode 32 are fixed inside the inspection tank 31 by an insulating jig 37.

Figure 9:
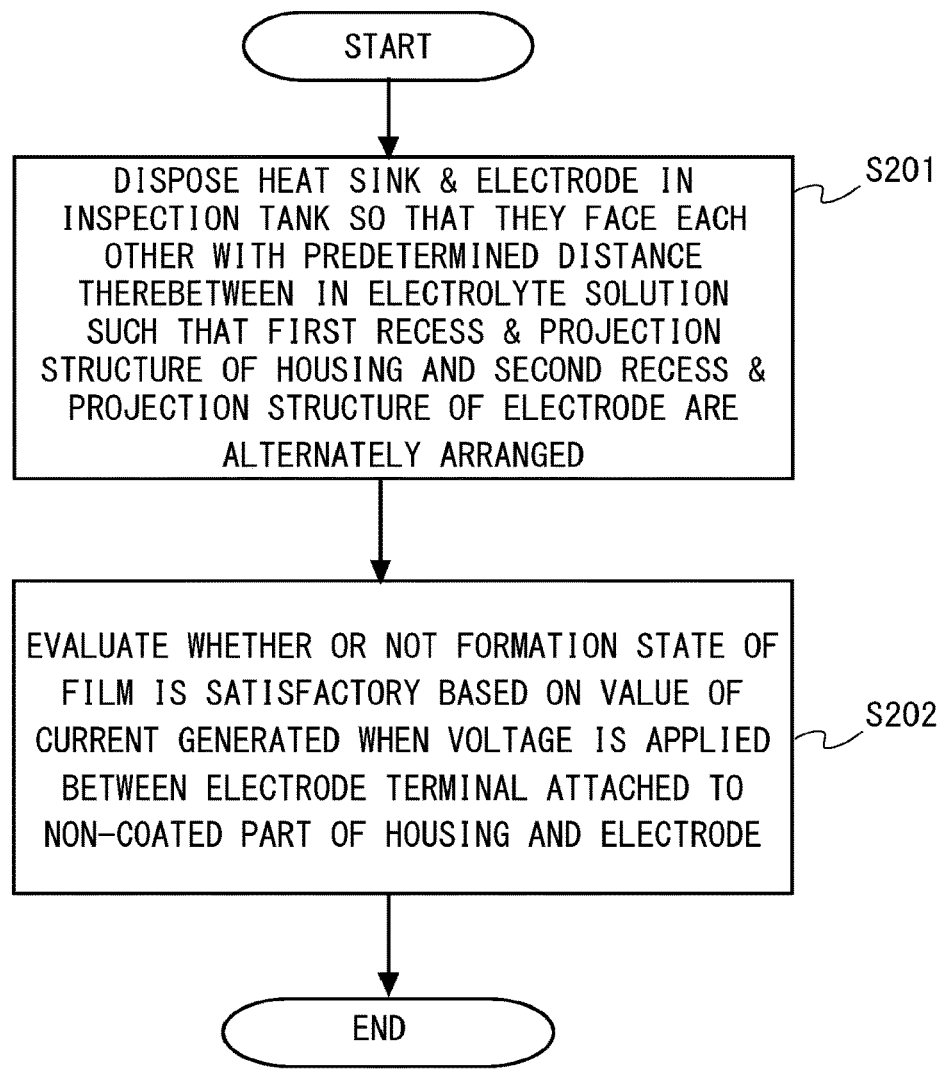
FIG. 9 is a flowchart showing a flow of a method for inspecting a heat sink according to the embodiment.

Next, a flow of a method for inspecting the heat sink 3 will be described with reference to FIG. 9. FIG. 9 is a flowchart showing a flow of the method for inspecting the heat sink 3. In the following description regarding the structure of the heat sink 3, refer to FIGS. 1 to 3 as appropriate.

Firstly, as shown in FIG. 9, the inspection electrode 32 is disposed to face the housing 8 in the electrolyte solution 36 with a predetermined distance therebetween in such a way that the cooling fins 8a and the electrode fins 32a are alternately arranged (Step S201). Next, a voltage is applied between the housing 8 and the inspection electrode 32, which have been arranged to face each other, and the formation state of the insulating film 9 is inspected based on the measured current value (Step S202). Prior to Step S201, the heat sink 3 may be cleaned by means such as ultrasonic cleaning. Moreover, after Step S202, ultrasonic cleaning may be performed to wash off the electrolyte solution 36 adhered to the heat sink 3.

In Step S201, if there is a defect generated in the insulating film 9 formed on the surface of the cooling fins 8a and in the gap bottom parts 8b between the cooling fins 8a, when a voltage is applied between the housing 8 and the inspection electrode 32, a current flows between an underlying metal part (surface of the housing 8) exposed due to the defect in the insulating film 9 and the inspection electrode 32 through the electrolyte solution 36. If an area of the underlying metal part exposed due to the defect in the insulating film 9 is relatively large, the current flowing between the exposed underlying metal part and the inspection electrode 32 becomes relatively large. On the other hand, if the area of the underlying metal part exposed due to the defect in the insulating film 9 is relatively small, the current flowing between the exposed underlying metal part and the inspection electrode 32 becomes relatively small. In other words, by measuring a value of the current flowing between the underlying metal part exposed due to the defect in the insulating film 9 and the inspection electrode 32 by using the ammeter 35, the formation state of the insulating film 9 can be inspected In Step A202, a voltage V applied between the electrode terminal 33 and the inspection electrode 32 by the power supply 34 is maintained substantially constant while measuring the current. In the inspection of the formation state of the insulating film 9, it may be evaluated as to whether or not the formation state of the insulation coating 9 is satisfactory by comparing the current value A measured by the ammeter 35 with a predetermined threshold Ath. That is, when the current value A measured by the ammeter 35 is equal to or less than the predetermined threshold value Ath ($A \leq Ath$), it is determined that the formation state of the insulating film 9 is satisfactory. On the other hand, when the current value A measured by the ammeter 35 is greater than the predetermined threshold Ath ($A > Ath$), it is determined that the formation state of the insulating film 9 is not satisfactory.

The voltage V may be adjusted so that the current value measured by the ammeter 35 exceeds a lower limit of the current value that can be detected by the ammeter 35. When the voltage V is adjusted in the inspection of the formation state of the insulating film 9, the evaluation of the formation state of the insulating film 9 may be performed by an inspector calculating a resistance R using the voltage V and the current value A measured by the ammeter 35 ($R=V/A$), and then comparing the calculated resistance value R with a predetermined threshold Rth. That is, if the calculated resistance R is equal to or greater than the threshold Rth ($R \geq Rth$), it is determined that the formation state of the insulating film is satisfactory. On the other hand, if the calculated resistance R is lower than the predetermined threshold Rth ($R < Rth$), it is determined that the formation state of the insulating film is not satisfactory.

Figure 10:
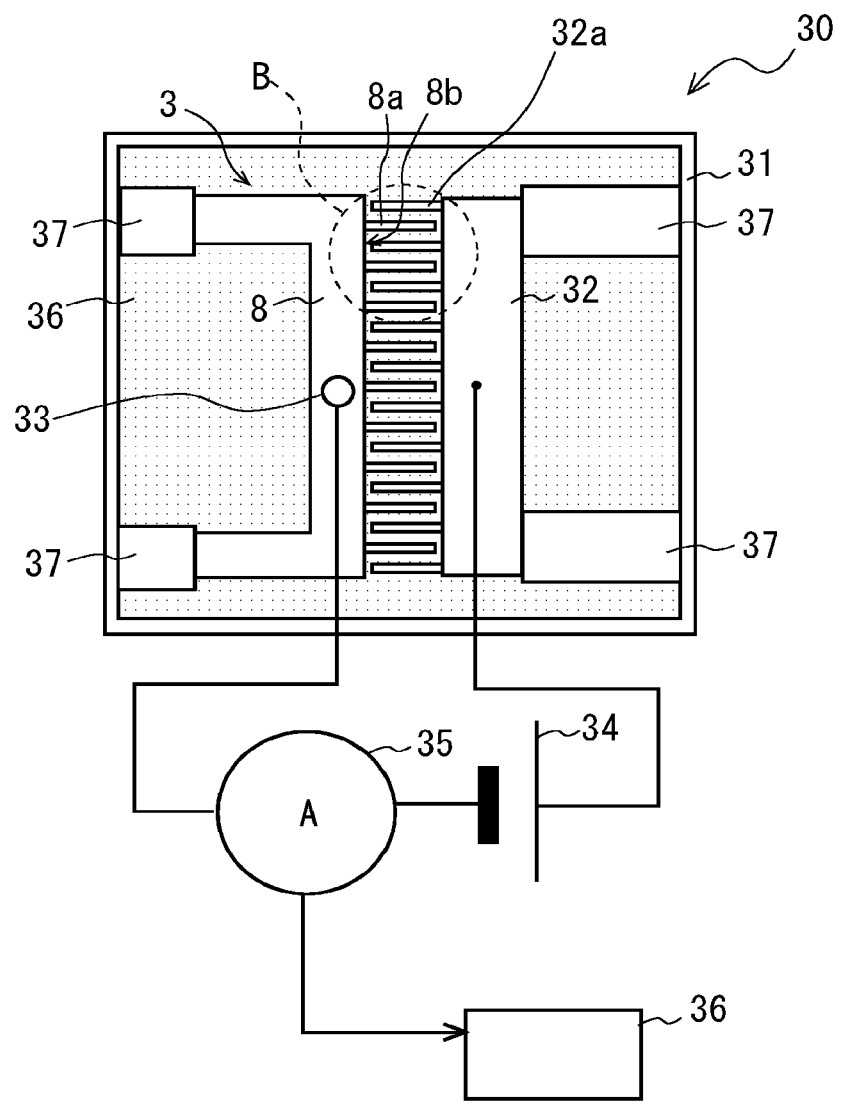
FIG. 10 is a drawing showing a case where the inspection apparatus for the heat sink according to this embodiment includes an evaluation unit for evaluating as to whether a formation state of an insulating film is satisfactory.

As shown in FIG. 10, the inspection apparatus 30 of the heat sink 3 may include an evaluation unit 36 that evaluates as to whether or not the formation state of the insulating film 9 is satisfactory.

In the method for inspecting the heat sink 3 according to this embodiment, the inspection electrode 32 including a plurality of electrode fins 32a that can be inserted between the cooling fins 8a and are arranged side by side is disposed to face the housing 8 with a predetermined distance therebetween in the electrolyte solution 36 in such a way that the cooling fins 8a and electrode fins 32a are alternately arranged. By arranging the inspection electrode 32 in this way, the distal ends of the electrode fins 32a, which are a part of the inspection electrode 32, can be brought close to the gap bottom parts 8b between the cooling fins 8a of the housing 8, in order to conduct an inspection. Thus, when there is a defect in the gap bottom parts 8b between the cooling fins 8a or in side surfaces of the cooling fins 8a, it is possible to accurately detect a value of a current flowing between a part where the surface of the housing 8 is exposed, which is the defect, and the electrode fins 32a. It is therefore possible to accurately inspect the formation state of the insulating film 9 and to reduce the cost as compared with the inspection method that detects individual defects using a visual inspection apparatus. Further, in the method for manufacturing the heat sink, as described above, by conducting the inspection of the heat sink capable of accurately inspecting the formation state of the insulating film while reducing the cost, it is possible to manufacture a heat sink with a satisfactory formation state of the insulating film without causing a significant increase in inspection cost.

Figure 11:
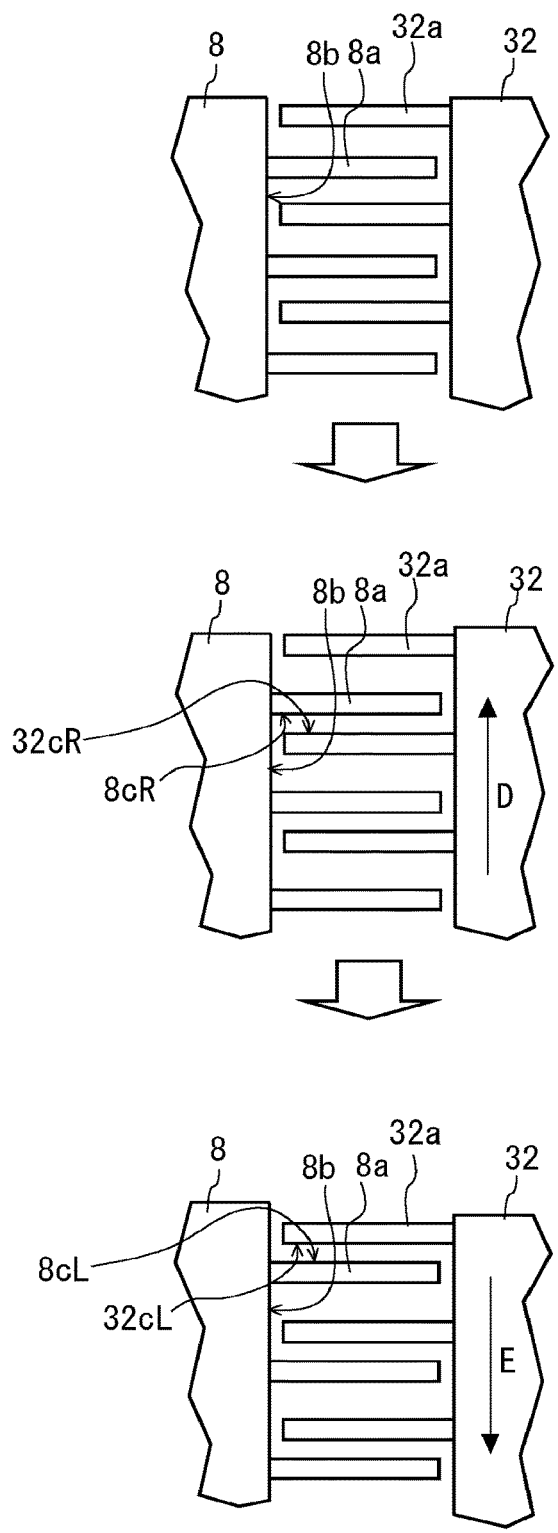
FIG. 11 is a drawing for describing a method for moving an electrode during current measurement in the method for inspecting the heat sink according to the embodiment.

When a voltage is applied between the housing 8 and the inspection electrode 32, which are arranged to face each other, the distance between the cooling fins 8a and electrode fins 32a may be changed as shown in FIG. 11 The distance between the cooling fins 8a and the electrode fins 32a may be changed by an actuator. When the inspection electrode 32 is moved in a direction (direction indicated by an arrow D in FIG. 11) in which the plurality of cooling fins 8a are arranged in the housing 8, a distance between side surface parts 8cR of the cooling fins 8a and respective side surface parts 32cR of the inspection electrode 32 becomes short. It is thus possible to accurately detect a defect in the side surface parts 8cR of the cooling fins 8a. When the inspection electrode 32 is moved in the direction (direction indicated by an arrow E in FIG. 11) opposite to that in which the plurality of cooling fins 8a are arranged in the housing 8, a distance between side surface parts 8cL of the cooling fins 8a and respective side surface parts 32cL of the inspection electrode 32 becomes short. It is thus possible to accurately detect a defect in the side surface parts 8cL of the cooling fins 8a.

Note that the present invention is not limited to the above embodiments, and modifications can be made without departing from the scope of the invention.

Figure 12:
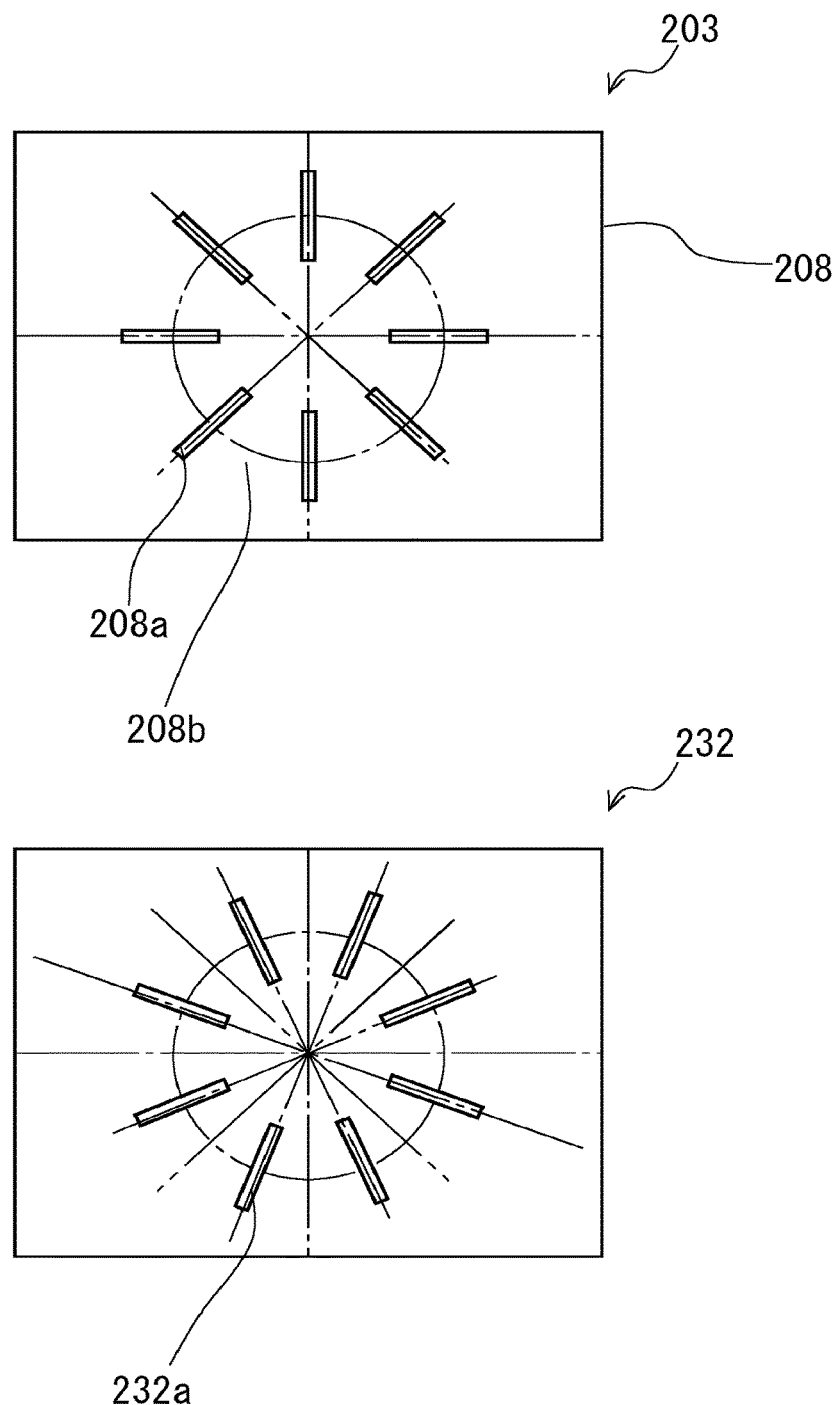
FIG. 12 is a drawing showing another example, which is different from that in FIG. 2, of an arrangement of a plurality of cooling fins on an outer surface of the housing.

In the above embodiment, as shown in FIG. 2, a plurality of cooling fins 8a are arranged in a comb-like manner on the outer surface of the housing 8. However, the heat sink to be inspected in the present invention is not limited to one including fins arranged in such a way. For example, as shown in FIG. 12, in a housing 208 of a heat sink 203, a plurality of cooling fins 208a may be radially arranged side by side with gap bottom parts 208b interposed therebetween. When the plurality of cooling fins 208a are arranged radially side by side with the gap bottom parts 208b interposed therebetween, electrode fins 232a in an inspection electrode 232 need to be radially arranged so that they can be inserted between the cooling fins 208a.

Figure 13:
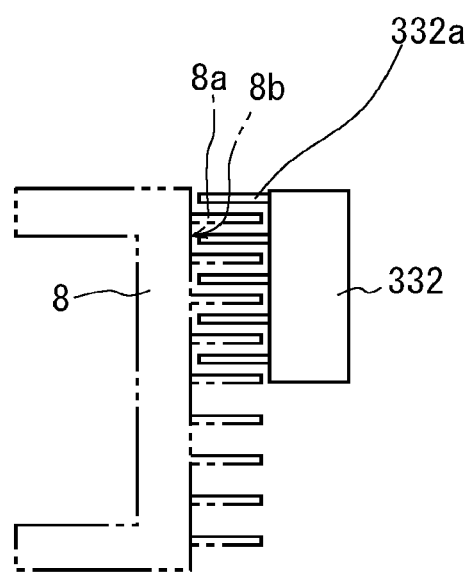
FIG. 13 is a drawing showing another example, which is different from that in FIG. 7, of an inspection electrode of the inspection apparatus used in the method for inspecting the heat sink according to the embodiment.
Figure 14:
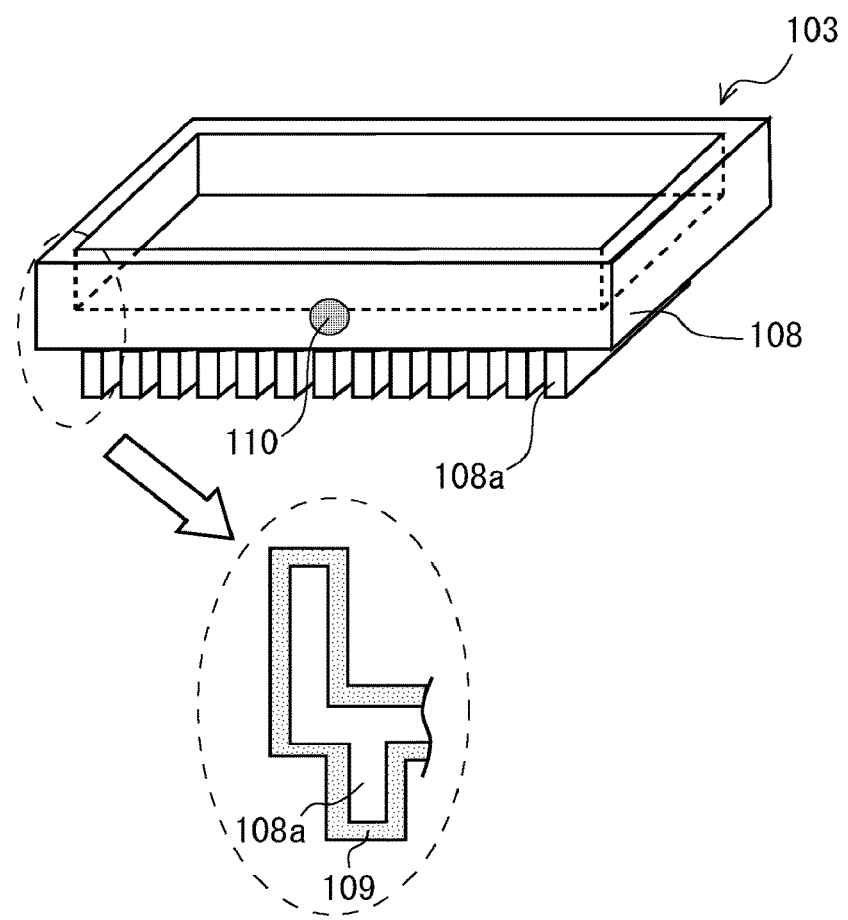
FIG. 14 is a perspective view showing a schematic structure of a heat sink developed by the inventors.
Figure 15:
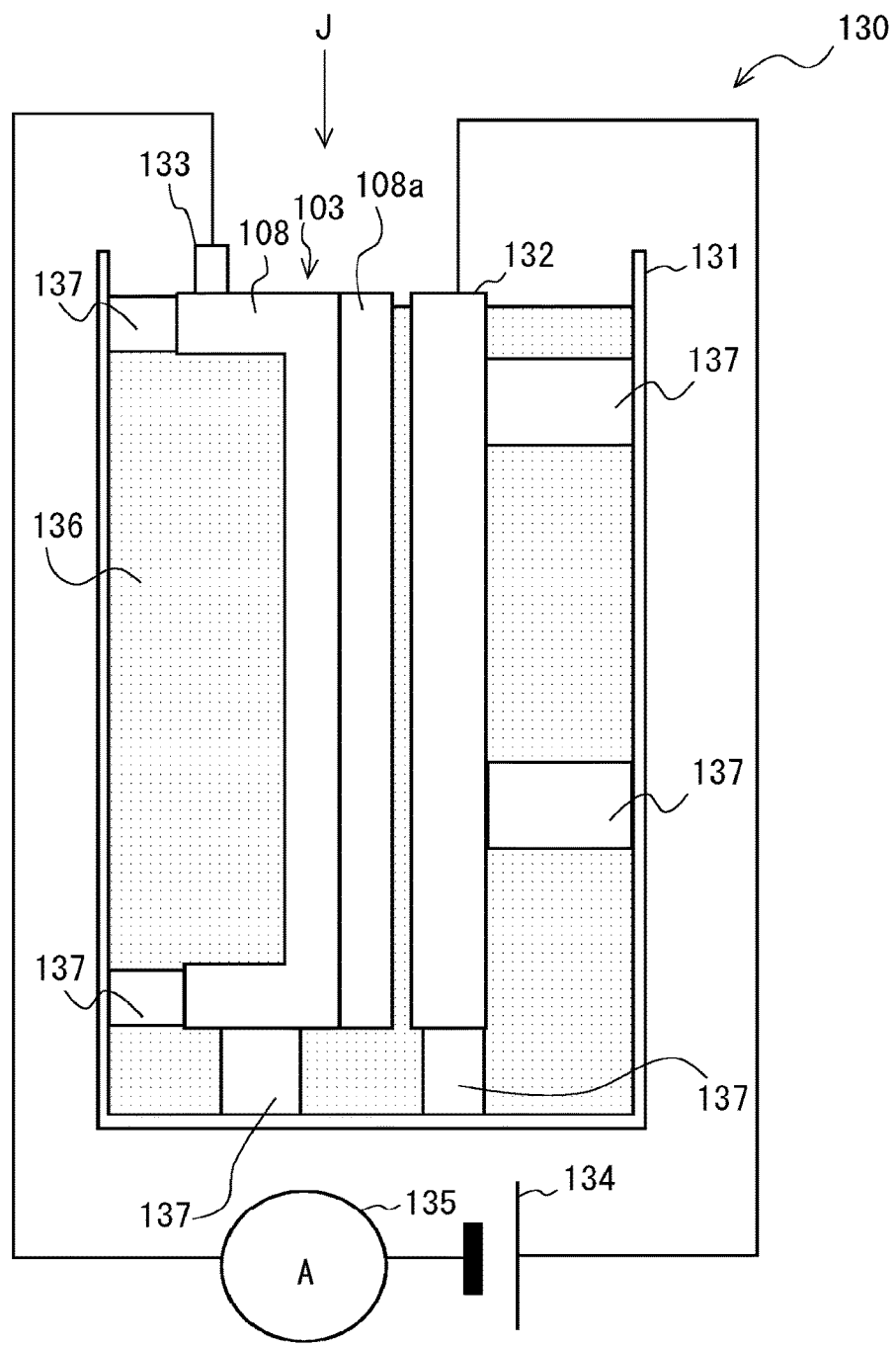
FIG. 15 is a perspective view showing a schematic structure of a prototype of an inspection apparatus for the heat sink developed by the inventors.
Figure 16:
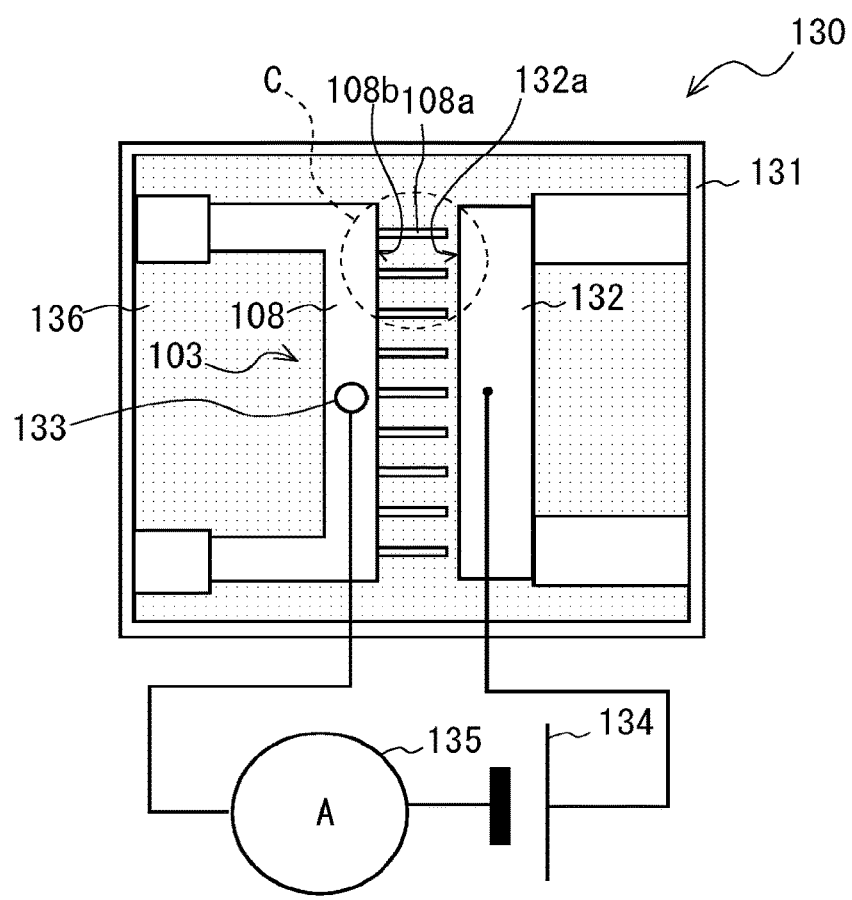
FIG. 16 is a drawing as seen from the direction indicated by an arrow J in FIG. 15.
Figure 17:
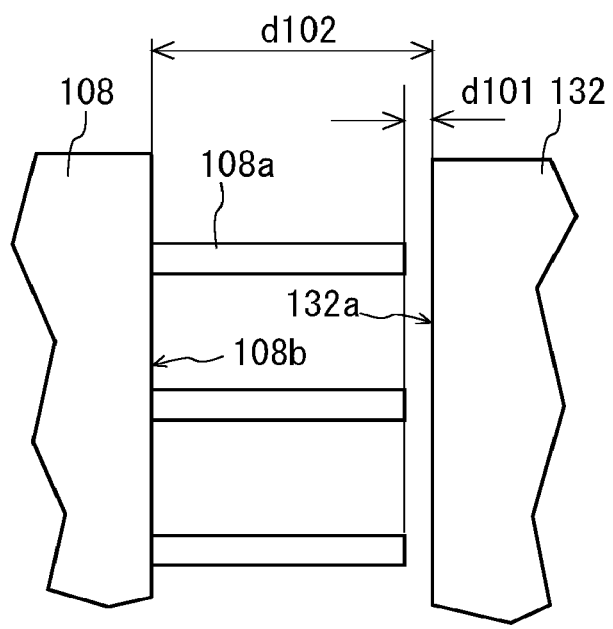
FIG. 17 is an enlarged view of a region C in FIG. 16.

In the above embodiment, as shown in FIG. 7, the electrode fins 32a are formed so that the electrode fins 32a are inserted between all of the cooling fins 8a of the inspection electrode 32. However, the electrode fins 32a are not limited to this. As shown in FIG. 13, the electrode fins 332a of an electrode 332 may be formed so that the electrode fins 332a are inserted only between some of the cooling fins 8a.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for inspecting a heat sink comprising a metallic housing including a plurality of first fins arranged side by side on an outer surface thereof, and an insulating film formed on a surface of the first fins and between the first fins, the method comprising:
    disposing, in an electrolyte solution, an inspection electrode including a plurality of second fins insertable between the first fins to face the housing with a predetermined distance therebetween in such a way that the first fins and the second fins are alternately arranged; and
    applying a voltage between the housing and the inspection electrode, which are arranged to face each other, and inspecting a formation state of the insulating film based on a measured value of a current.

2. The method according to claim 1, wherein a distance between the first fins and the second fins is changed when the voltage is applied between the housing and the inspection electrode that are arranged to face each other.

3. The method according to claim 1, wherein the formation state of the insulating film is determined to be not satisfactory when the measured value of the current is greater than a predetermined threshold.

4. An inspection apparatus for a heat sink comprising a metallic housing including a plurality of first fins arranged side by side on an outer surface thereof, and an insulating film formed on a surface of the first fins and between the first fins, the inspection apparatus comprising:
    an inspection electrode including a plurality of second fins insertable between the first fins; and
    an ammeter configured to measure a value of a current flowing between the housing and the inspection electrode, wherein
    in an electrolyte solution, the inspection electrode is disposed to face the housing with a predetermined distance therebetween in such a way that the first fins and the second fins are alternately arranged, a voltage is applied between the housing and the inspection electrode, and a formation state of the insulating film is inspected based on a measured value of a current.

5. The inspection apparatus according to claim 4, further comprising an evaluation unit configured to evaluate the formation state of the insulating film, the formation state of the insulating film being determined to be not satisfactory when the measured value of the current is greater than a predetermined threshold.

6. A method for manufacturing a heat sink comprising a metallic housing including a plurality of first fins arranged side by side on an outer surface thereof, and an insulating film formed on a surface of the first fins and between the first fins, the method comprising:
    forming the housing;
    forming the insulating film on the surface of the first fins and between the first fins;
    disposing, in an electrolyte solution, an inspection electrode including a plurality of second fins insertable between the first fins to face the housing with a predetermined distance therebetween in such a way that the first fins and the second fins are alternately arranged; and
    applying a voltage between the housing and the inspection electrode, which are arranged to face each other, and inspecting a formation state of the insulating film based on a measured value of a current.

7. The method according to claim 6, wherein the formation state of the insulating film is determined to be not satisfactory when the measured value of the current is greater than a predetermined threshold.

\* \* \* \* \*